US008846651B2

(12) United States Patent
Ishida et al.

(10) Patent No.: US 8,846,651 B2
(45) Date of Patent: Sep. 30, 2014

(54) LIPID COMPOSITION HAVING EXCELLENT SHAPE RETENTION PROPERTY AND PRODUCT

(75) Inventors: Kenya Ishida, Hiratsuka (JP); Chiyomi Birou, Hiratsuka (JP); Tetsuya Yamamoto, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 462 days.

(21) Appl. No.: 12/529,272

(22) PCT Filed: Feb. 27, 2008

(86) PCT No.: PCT/JP2008/053445
§ 371 (c)(1),
(2), (4) Date: Aug. 31, 2009

(87) PCT Pub. No.: WO2008/105475
PCT Pub. Date: Sep. 4, 2008

(65) Prior Publication Data
US 2010/0093682 A1      Apr. 15, 2010

(30) Foreign Application Priority Data
Mar. 1, 2007   (JP) ................. 2007-052067

(51) Int. Cl.
*A61K 31/568* (2006.01)
*A61Q 19/00* (2006.01)
*A24B 15/10* (2006.01)
*A61K 8/18* (2006.01)
*C11D 3/20* (2006.01)
*C09K 3/00* (2006.01)
*A61K 8/63* (2006.01)
*A23L 1/30* (2006.01)
*A24B 15/30* (2006.01)
*A61K 47/28* (2006.01)
*A23L 1/226* (2006.01)
*A61K 8/34* (2006.01)

(52) U.S. Cl.
CPC . *A61K 47/28* (2013.01); *A61K 8/63* (2013.01); *A23L 1/3004* (2013.01); *A24B 15/30* (2013.01); *A61Q 19/00* (2013.01); *A23L 1/2265* (2013.01); *A61K 8/34* (2013.01); *A23V 2002/00* (2013.01)
USPC ............. 514/171; 131/352; 512/19; 510/130; 252/182.1

(58) Field of Classification Search
None
See application file for complete search history.

(56) References Cited

U.S. PATENT DOCUMENTS

| 3,023,253 | A |   | 2/1962 | Bain et al. |
| 3,064,311 | A |   | 11/1962 | Bain et al. |
| 5,352,437 | A | * | 10/1994 | Nakagawa et al. .............. 424/45 |
| 5,626,854 | A | * | 5/1997 | Ichii et al. ....................... 424/401 |
| 6,328,982 | B1 | * | 12/2001 | Shiroyama et al. ............ 424/401 |
| 2005/0169987 | A1 |   | 8/2005 | Korber |

FOREIGN PATENT DOCUMENTS

| EP | 1 023 842 | A2 |   | 8/2000 |   |
| EP | 1 486 204 | A1 |   | 12/2004 |   |
| JP | 63-192703 | A |   | 8/1988 |   |
| JP | 3-072433 | A |   | 3/1991 |   |
| JP | 5-163136 | A |   | 6/1993 |   |
| JP | 7-002631 | A |   | 1/1995 |   |
| JP | 7-313092 | A |   | 12/1995 |   |
| JP | 9-125087 | A |   | 5/1997 |   |
| JP | 2000-217538 | A |   | 8/2000 |   |
| JP | 2004-026750 | A |   | 1/2004 |   |
| JP | 2004-035802 | A |   | 2/2004 |   |
| JP | 2005-206524 | A | * | 4/2005 | ............... A61K 7/06 |
| JP | 2005-206524 | A |   | 8/2005 |   |
| JP | 2005-528436 | A |   | 9/2005 |   |
| WO | 03/074622 | A1 |   | 9/2003 |   |
| WO | 03/077891 | A1 |   | 9/2003 |   |

OTHER PUBLICATIONS

"Health Benefits of Peppermint Oil" (www.organicfacts.net/organic-oils/natural-essential-oils/health-benefits-of-peppermint-oil.html).*
International Search Report for PCT/JP2008/053445, dated Apr. 22, 2008.
International Preliminary Report on Patentability for PCT/JP2008/053445, dated Apr. 22, 2008.
Chinese Patent Office, Office Action, dated Mar. 16, 2011, issued in Application No. 200880006780.3
Chinese Patent Office, Office Action dated Sep. 8, 2011, issued in counterpart Chinese Application No. 200880006780.3.
Japanese Patent Office, Communication dated Mar. 26, 2013, issued in corresponding Japanese Patent Application No. 2008-048872.

* cited by examiner

*Primary Examiner* — Dennis Heyer
(74) *Attorney, Agent, or Firm* — Sughrue Mion, PLLC

(57) ABSTRACT

It is to provide a technique for preventing aggregation or caking of menthol at the time of its keeping. In addition, it is to provide a lipid composition, which can show excellent thermal stability even in the case of high temperature at the time of keeping menthol and at the time of blending in a product, does not cause mutual aggregation of powders, particles, flakes, pellets, sticks and the like of menthol, and can maintain its shape retention property. From 10 to 50% by mass of sterols are added to and mixed with from 50 to 90% by mass of menthol, and the resultant is melted with heating. Paraffins may be further added and mixed in an amount of 20% by mass or less, based on the lipid composition.

11 Claims, No Drawings

US 8,846,651 B2

LIPID COMPOSITION HAVING EXCELLENT SHAPE RETENTION PROPERTY AND PRODUCT

TECHNICAL FIELD

The present invention relates to a lipid composition having excellent shape retention property, a product constituted from said lipid composition and a product comprising said lipid composition. In particular, the invention relates to a lipid composition having excellent shape retention property, which consists essentially of menthol and sterols and, a product which is constituted from said lipid composition and is selected from food or drink, toiletry products, fragrance or cosmetic, bathing agents, pharmaceutical and tobacco, a product which comprises said lipid composition, and a product which comprises the same and is selected from food or drink, toiletry products, fragrance or cosmetic, bathing agents and pharmaceutical.

BACKGROUND OF THE INVENTION

Menthol has been broadly used for a long time because of its characteristics in that it has a special cool fragrance or flavor and can provide refresh-feeling. Presently, it is frequently used in the field of a lip cream or the like fragrance or cosmetic, a compounding agent of a pharmaceutical agent which alleviates muscular ache and the like symptoms, and the like.

Menthol is naturally extracted from peppermint oil of a mint which is a perennial plant of Lamiaceae. On the other hand, methods for chemically synthesizing menthol have also been actively studied and developed, and a large number of synthesizing methods are known.

Menthol is kept in the form of a powdery, a granular, a flake-like, a pellet-like and a stick-like and the like shapes, and as occasion demands, pulled out from the keeping place and blended in a product. In that case, there is a problem of causing spoilage of its handling property due to aggregation of menthol at the time of its keeping, so that concern has been directed toward the development of techniques for solving the problem. As one of such techniques, a technique for applying a compression treatment to menthol under a compression pressure of 50 kN has been reported (Patent Reference 1). It may be said that this method is surely excellent in terms of aggregation or caking, in comparison with the case of the compression-untreated menthol, but it is not at a degree which is sufficiently satisfactory. Particularly, this was not sufficient for satisfying thermal stability during summer season. In addition, since a compressor is used, this is economically disadvantageous in terms of its purchase, maintenance, management and the like, and its operational troublesomeness also remains.

Patent Reference 1: JP-T-2005-528436 (the term "JP-T" as used herein means a published Japanese translation of a PCT patent application)

DISCLOSURE OF THE INVENTION

Problems that the Invention is to Solve

Accordingly, concern has been directed toward the development of a technique which can prevent aggregation and the like of menthol at the time of its keeping, by a simple operation and to a satisfactory level. The problem of the invention is to provide a technique which can respond to such a demand. That is, it is to provide a technique for preventing aggregation or caking of menthol at the time of its keeping. In addition, it is to provide a technique which can show excellent stability even in the case of high temperature at the time of keeping menthol and at the time of processing into a product and which does not cause mutual aggregation of powders, particles, flakes, pellets and sticks of menthol.

Means for Solving the Problems

While carrying out many studies for purposes of solving the aforementioned problem, the present inventors have obtained knowledge contrary to expectations that a eutectic mixture of menthol and sterols can excellently solve the above-mentioned problem. By further carrying out studies based on this unexpected knowledge, the invention has been finally accomplished.

That is, the invention includes the following inventions.

(1) A lipid composition having excellent shape retention property, which comprises a menthol and a sterols.

(2) The lipid composition according to (1), which comprises the menthol in an amount of from 50 to 90% by mass and the sterols in an amount of from 10 to 50% by mass.

(3) The lipid composition according to (1) or (2), which further comprises a paraffins.

(4) The lipid composition according to (3), wherein a content of the paraffins is 20% by mass or less based on the lipid composition.

(5) The lipid composition according to any one of (1) to (4), which further comprises at least one or more kinds of materials selected from the group consisting of menthone, camphor, pulegol, 1-isopulegol, 3-(1-menthoxy)propane-1,2-diol, 2-(1-menthoxy)ethan-1-ol, 3-(1-menthoxy)propan-1-ol, 2-methyl-3-(1-menthoxy)propane-1,2-diol, 2-[(1-menthoxy)ethoxy]-ethanol, N-ethyl-1-menthylcarboxamide, p-menthane-3,8-diol, 1-menthyl lactate, N-methyl-(2,2-isopropylmethyl-3-methylbutanamide, vanillyl ethers, capsaicine, salicylic acid esters, mint oil, peppermint oil and spearmint.

(6) The lipid composition according to any one of (1) to (5), wherein a content of the material is 20% by mass or less based on the lipid composition.

(7) A food or drink, which comprises the lipid composition according to any one of (1) to (6).

(8) A toiletry product, which comprises the lipid composition according to any one of (1) to (6).

(9) A fragrance or cosmetic, which comprises the lipid composition according to any one of (1) to (6).

(10) A bathing agent, which comprises the lipid composition according to any one of (1) to (6).

(11) A pharmaceutical, which comprises the lipid composition according to any one of (1) to (6).

(12) A tobacco, which comprises the lipid composition according to any one of (1) to (6).

(13) A eutectic mixture having excellent shape retention property, which comprises a menthol and a sterols.

Advantage of the Invention

By the invention, it was able to provide a lipid composition which is excellent in thermal stability and comprises high menthol content. This lipid composition does not aggregate or only slightly aggregates, even when it is kept under a relatively high temperature. In addition, even when these lipid compositions are added to food or drink, toiletry products, fragrance or cosmetic, bathing agents, pharmaceutical or tobacco, aggregation of the menthol-containing products hardly occurs, which is advantageous from the viewpoint of workability.

BEST MODE FOR CARRYING OUT THE INVENTION

The following describes the invention in detail.

One of the components contained in the lipid composition of the invention is menthol. Menthol is an already known substance. According to the invention, menthol may be an optically active substance or racemic substance, but is desirably 1-menthol alone. In this connection, an isomer other than 1-menthol may be coexisted with 1-menthol. In addition, it may be dl-menthol instead of 1-menthol. Amount of the above-mentioned isomer other than 1-menthol is not particularly limited.

Though the shape of menthol is not particularly limited, menthol having an optimum shape may be optionally used in response to the necessity. In this connection, as the shape of menthol, for example, there are a powdery, a granular, a flake-like, a pellet-like, a stick-like and the like, though not limited thereto. In addition, it may be a crystal of menthol or may be its amorphous form.

Sterols are other component contained in the lipid composition of the invention. Such sterols are compounds having a backbone represented by the following formula 1, which are compounds having from 27 to 30 carbon atoms. That is, the sterols mean a compound represented by the formula 1, a derivative thereof, their glycosides or their mixtures. In this case, said derivative means a compound in which a hydrogen atom of the compound represented by the formula 1 is substituted by an alkyl group or the like organic group.

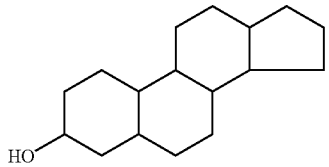

(Formula 1)

The aforementioned sterols are already known compounds. As the aforementioned sterols, for example, cholesterol, phytosterol, ergosterol, stigmasterol, campesterol, spinasterol, brassicasterol and the like can be cited. Particularly, cholesterol and phytosterol are desirable, and cholesterol is more desirable. As the sterols, one kind thereof may be used alone, or two or more kinds thereof may be used in combination.

The lipid composition of the invention desirably contains menthol in an amount of from 50 to 90% by mass and sterols in an amount of from 10 to 50% by mass, more desirably contains menthol in an amount of from 50 to 80% by mass and sterols in an amount of from 20 to 50% by mass, and particularly desirably contains menthol in an amount of from 50 to 70% by mass and sterols in an amount of from 30 to 50% by mass. By controlling menthol and sterols at said ratio, a lipid composition having superior shape retention property can be prepared. In addition, the shape retention property cannot be maintained when the sterols are contained in an amount of less than 10% by mass, and a uniform mixture cannot be obtained when the sterols are contained in an amount of more than 50% by mass, so that a eutectic mixture cannot be obtained.

The lipid composition of the invention can be prepared by heating menthol and sterols and thereby making them into a eutectic mixture. That is, the lipid composition of the invention includes a molten product obtained by heating menthol and sterols.

The aforementioned heating condition is not particularly limited, and any condition may be set with the proviso that a lipid composition molten product (to be referred to as lipid composition in some cases hereinafter) of the menthol and aforementioned sterols can be formed. Though the heating temperature cannot be defined in a wholesale manner because it varies depending on the kinds and amounts of menthol and sterols to be used, it is required to set the temperature to a level of equal to or higher than the temperature at the time when a portion of menthol or sterols starts to melt, and it is generally desirable to carry out the heating at a temperature of equal to or higher than the melting point of menthol.

Illustratively, it is desirable to carry out the heating, for example, at a range of from 40 to 120° C. under normal pressure. Further, it is more desirable to carry out the heating at a range of from 45 to 110° C. under normal pressure, and it is particularly desirable to carry out the heating at a range of from 50 to 100° C. under normal pressure. Regarding the heating period of time, it cannot be defined in a wholesale manner, because it varies depending on the kinds and amounts of the menthol and sterols to be used and the heating conditions.

Though the lipid composition of the invention consists essentially of menthol and sterols, it may further contain paraffins. The paraffins as described herein are chain saturated hydrocarbons and compounds having 30 or less carbon atoms. It is desirable that the amount of such paraffins in the lipid composition is set to 20% by mass or less based on the lipid composition to be prepared. When such paraffins are present in the lipid composition, a suitable effect can be induced in terms of the shape retention property.

The lipid composition of the invention may contain at least one or more kinds selected from the group consisting of menthone, camphor, pulegol, 1-isopulegol, 3-(1-menthoxy)propane-1,2-diol, 2-(1-menthoxy)ethan-1-ol, 3-(1-menthoxy)propan-1-ol, 2-methyl-3-(1-menthoxy)propane-1,2-diol, 2-[(1-menthoxy)ethoxy]-ethanol, N-ethyl-1-menthylcarboxamide, p-menthane-3,8-diol, 1-menthyl lactate, N-methyl-(2,2-isopropylmethyl-3-methylbutanamide, vanillyl ethers, capsaicine, salicylic acid esters, mint oil, peppermint oil and spearmint. These materials are already known.

It is desirable that the amount of the aforementioned material in the lipid composition is set to 20% by mass or less based on the lipid composition to be prepared. When the aforementioned material is present in the lipid composition, cool-feeling and refresh-feeling can be further improved.

The lipid composition of the invention is excellent in shape retention property and further possesses of cool-feeling (refresh-feeling). The shape retention property in this case means a property in which menthol or a lipid composition containing menthol maintains its shape thermally stably. For example, it means that when prepared into a stick-like, pellet-like, flake-like or the like shape, its shape is maintained at the melting point of menthol (e.g., 45° C.) or more, illustratively even after 24 hours of standing at 50° C. In addition, it also means that when menthol or a lipid composition containing menthol is used, its shape is maintained to such a degree that, for example, its operability does not become inconvenient.

The lipid composition of the invention can be used by processing it into, for example, a powdery, a granular, a flake-like, a pellet-like and a stick-like and the like shapes.

The processing method is not particularly limited, and these can be prepared by optionally making use of known methods. As the processed shape, for example, a powdery, a granular, a flake-like, a pellet-like, a stick-like and the like can be cited, of which a flake-like, a pellet-like and a stick-like are preferable.

A lipid composition processed into the aforementioned shape can be blended in a product directly as its shape, and as illustrative examples of the product, food or drink, toiletry products, fragrance or cosmetic, bathing agents, pharmaceutical, tobacco and the like can be cited. The blending amount into these products cannot be defined in a wholesale manner, because it varies depending on the kinds and blending amounts of the compounds to be used in preparing the lipid composition, the processing shapes and the like. In boldly describing, for example, the amount is approximately 40% by mass or more in a product based on the product. In addition, according to the invention, even in the case of a product consisting of 100% by mass of a lipid composition, it can be made into the product because it is excellent in the shape retention property.

In addition, a compounding agent can be blended in advance in object products in which menthol is blended, in which the object products are generally used in food or drink, toiletry products, fragrance or cosmetic, bathing agents, pharmaceutical, tobacco and the like, which comprises the lipid composition of the invention.

As the aforementioned compounding agent, it is not particularly limited, but in illustratively exemplifying, for example, a surfactant, an oil solution, a monovalent alcohol, a fragrance or flavor, a dye compound, a reducing agent, an oxidizing agent, a metal chelating agent, an antioxidant, a viscosity adjusting agent, an antiseptic, an animal or plant extract, an anti-inflammatory drug, a germicide, an oxidation inhibitor, a pearly sheen agent, an ultraviolet ray absorbent, a moisture keeping agent, an organic or inorganic salt, a pH controller and a pigment can be cited.

The lipid composition of the invention (to be referred sometimes to as composition hereinafter) can be blended in food or drink, toiletry products, fragrance or cosmetic, bathing agents, pharmaceutical, tobacco and the like.

As the aforementioned food or drink, it is not particularly limited, but for example, processed foods which use livestock meats, chicken meats, fishes and shellfishes and the like as the materials, soups, seasonings, dried seasoning powders, convenience food, snack foods, canned foods, milk products, sweets, frozen deserts, and tea, coffee, vegetable juice, green juice and the like drinks can be cited.

The blending amount of the composition of the invention in the food or drink cannot be defined in a wholesale manner, because it varies depending on the kinds of materials contained in the composition, kinds of the food or drink, and the like. In boldly describing, it is desirable to set the amount to, for example, approximately from 0.001 to 40% by mass, and it is more desirable to set the amount to approximately from 0.01 to 10% by mass, based on the food or drink.

Though the aforementioned toiletry products and fragrance or cosmetic are not particularly limited, their examples include pomade, brilliantine, set lotion, hair stick, hair solid, hair oil, hair treatment, hair cream, hair tonic, hair liquid, hair spray, bandoline, hair tonic, hair dye and the like hair cosmetics; shampoo, rinse, rinse in shampoo, conditioner, treatment, hair pack and the like hair care products; perfume, eau de parfum, eau de toilette, cologne and the like fragrance products; cleansing cream, vanishing cream, cleansing cream, cold cream, massage cream, milky lotion, face lotion, beauty liquid, pack, make remover and the like foundation cosmetics; foundation, face powder, solid powder, talcum powder, lipstick, lip cream, rouge, eye liner, mascara, eye shadow, eyebrow, eye pack, nail enamel, enamel remover and the like finishing cosmetics; antiperspirant, after-shaving lotion, jell, permanent wave agent, medicated soap, medicated shampoo, medicated skin cosmetic and the like medicinal cosmetics; toilet soap, bath soap, perfume soap, transparent soap, synthetic soap and the like soaps; body soap, body shampoo, hand soap and the like body lotions; heavy duty detergent for clothing, light duty detergent for clothing, liquid detergent, washing soap, compact detergent, powder soap and the like detergents; softener, furniture care and the like soft finishing preparations; and kitchen soap, kitchen synthetic soap, tableware detergent and the like kitchen detergents.

The blending amount of the composition of the invention in the toiletry products or fragrance or cosmetic cannot be defined in a wholesale manner, because it varies depending on the kinds of materials contained in the composition, kinds of the toiletry products or fragrance or cosmetic, and the like. In boldly describing, it is desirable to set the amount to, for example, approximately from 0.001 to 40% by mass, and it is more desirable to set the amount to approximately from 0.01 to 10% by mass, based on the toiletry product. Also, it is desirable to set the amount to, for example, approximately from 0.001 to 40% by mass, and it is more desirable to set the amount to approximately from 0.01 to 10% by mass, based on the fragrance or cosmetic.

The composition of the invention can also be blended in an oral product. As the oral product, it is not particularly limited, but for example, oral cleaner, mouth wash and the like can be cited.

The blending amount of the composition of the invention in the oral product cannot be defined in a wholesale manner, because it varies depending on the kinds of materials contained in the composition, kinds of the oral product, and the like. In boldly describing, it is desirable to set the amount to, for example, approximately from 0.001 to 40% by mass, and it is more desirable to set the amount to approximately from 0.01 to 10% by mass, based on the oral product.

As the above-mentioned bathing agents, it is not particularly limited, but for example, bath salt, bath tablet, bath liquid and the like can be cited. As the above-mentioned pharmaceutical, it is not particularly limited, but for example, adhesive skin patch, ointments and the like skin external preparations and internal preparations and the like can be cited.

The blending amount of the composition of the invention in the bathing agent or pharmaceutical cannot be defined in a wholesale manner, because it varies depending on the kinds of materials contained in the composition, the components contained in the bathing agents or pharmaceutical, and the like. In boldly describing, it is desirable to set the amount to, for example, approximately from 0.001 to 40% by mass, and it is more desirable to set the amount to approximately from 0.01 to 10% by mass, based on the bathing agent. Also, it is desirable to set the amount to, for example, approximately from 0.001 to 40% by mass, and it is more desirable to set the amount to approximately from 0.01 to 10% by mass, based on the pharmaceutical.

As the above-mentioned tobacco, it is not particularly limited, but for example, cigarette, cigar, sniff (snuff), chewing tobacco and the like can be cited.

The blending amount of the composition of the invention in the tobacco cannot be defined in a wholesale manner, because it varies depending on the kinds of materials contained in the composition, the components contained in the tobacco, and the like. In boldly describing, in the case of a cigarette for example, when added to a cut tobacco, a roll of paper, a filter or the like, it is desirable to set the adding amount as the menthol unit to approximately from 0.01 to 20% by mass, it is more desirable to set the amount to approximately from 0.1 to 5% by mass, though it depends on the blending ratio of menthol and sterol; in the case of a cigar, when added to a cut tobacco or the like, it is desirable to set the adding amount as the menthol unit to approximately from 0.01 to 20% by mass, it is more desirable to set the amount to approximately from 0.1 to 5% by mass; when added to a sniff (snuff), and it is desirable to set the adding amount as the menthol unit to approximately from 0.001 to 20% by mass, it is more desirable to set the amount to approximately from 0.01 to 5% by mass; and when added to a chewing tobacco, it is desirable to set the adding amount as the menthol unit to approximately from 0.001 to 20% by mass, and it is more desirable to set the amount to approximately from 0.01 to 5% by mass.

EXAMPLES

The following describes the invention in detail based on examples, but the invention is not limited to these examples.

Examples 1 to 4

Preparation of Lipid Compositions

Predetermined amounts of menthol and cholesterol were weighed to realize the component ratios described in Table 1, mixed in a container and then subjected to a heating treatment at from 50 to 100° C. under normal pressure, thereby obtaining a eutectic mixture of the menthol and cholesterol. By solidifying the mixture at room temperature, respective lipid compositions were prepared.

Melting points of the lipid compositions of Examples 1 to 4 were as shown in Table 1. In this case, the melting point was measured at from 30 to 80° C. (1° C./minute) using an automatic melting point apparatus (METTLER TOLEDO-FP900).

TABLE 1

| No. | l-Menthol | Cholesterol | Melting point (° C.) |
| --- | --- | --- | --- |
| Example 1 | 50 | 50 | 70.2 |
| Example 2 | 70 | 30 | 63.6 |
| Example 3 | 80 | 20 | 59.4 |
| Example 4 | 90 | 10 | 45.6 |

Comparative Example 1

As Comparative Example 1, predetermined amounts of l-menthol and cholesterol were weighed to realize the component ratio described in Table 2, and the subsequent operations were carried out in the same manner as in Examples 1 to 4, but a uniform mixture was not formed so that it was not able to obtain a eutectic mixture.

Comparative Examples 2 and 3

As Comparative Example 2, predetermined amounts of l-menthol and cholesterol were weighed to realize the component ratio described in Table 2, and the subsequent operations were carried out in the same manner as in Examples 1 to 4 to obtain a lipid composition. Also, as Comparative Example 3, the same operations of Examples 1 to 4 were carried out except that cholesterol was not used and l-menthol alone was used, thereby obtaining a lipid composition.

Test Example 1

The lipid compositions of Examples 1 to 4 and Comparative Examples 2 and 3 were melted with heating, solidified at room temperature and then kept in a constant temperature oven at 50° C. for 24 hours, and their respective shape retention property was judged by evaluating the appearance by 10 panelists based on the following evaluation criteria. As Comparative Example 1, a lipid composition was obtained by weighing predetermined amounts of l-menthol and cholesterol to realize the component ratio described in Table 2, and carrying out the subsequent operations in the same manner as in Examples 1 to 4. As Comparative Example 2, a lipid composition was obtained by carrying out the same operations of Examples 1 to 4, except that cholesterol was not used and l-menthol alone was used. The measured results are shown in Table 2.

Evaluation Criteria

A No change in the solid condition

B Hardness is slightly reduced, but the solid condition is maintained

C Fluidity is observed, and the solid condition is difficult to be maintained

D Fluidity is high, and the solid condition cannot be maintained

In this connection, the evaluation results in Table 2 represent evaluation results by the most frequent panelists.

TABLE 2

| No. | l-Menthol | Cholesterol | Evaluation results |
| --- | --- | --- | --- |
| Example 1 | 50 | 50 | A |
| Example 2 | 70 | 30 | A |
| Example 3 | 80 | 20 | B |
| Example 4 | 90 | 10 | B |
| Comparative Ex. 1 | 40 | 60 | — |
| Comparative Ex. 2 | 95 | 5 | D |
| Comparative Ex. 3 | 100 | 0 | D |

Examples 5 to 12

Preparation of Compositions

Lipid compositions were prepared by weighing predetermined amounts of menthol and the sterols described in Table 3 to realize the component ratios described in Table 3, mixing them in respective containers and then carrying out the operations in the same manner as in Example 1. The lipid compositions of Examples 5 to 12 were manipulated in the same manner as in Test Example 1, and their respective shape retention property was judged. The measured results are shown in Table 3.

Examples 13 to 17

Preparation of Compositions

Lipid compositions were prepared by weighing predetermined amounts of the menthol, the sterols described in Table 3 and paraffin to realize the component ratios described in Table 3, mixing them in respective containers and then carrying out the operations in the same manner as in Example 1. The lipid compositions of Examples 13 to 17 were manipulated in the same manner as in Test Example 1, and their respective shape retention property was judged. The measured results are shown in Table 3.

In Table 3, Ceresine 810 (manufactured by NIKKO RICA CORPORATION) was used as the paraffin.

TABLE 3

| | Examples | | | | | | | | | | | | |
|---|---|---|---|---|---|---|---|---|---|---|---|---|---|
| | 5 | 6 | 7 | 8 | 9 | 10 | 11 | 12 | 13 | 14 | 15 | 16 | 17 |
| l-Menthol | 75 | 80 | 70 | 70 | 70 | 70 | 70 | 50 | 70 | 70 | 75 | 70 | |
| dl-Menthol | | | | | | | | | | | | | 70 |
| Cholesterol | 25 | | | | | | | | 20 | 15 | 20 | 10 | 30 |
| Phytosterol | | 20 | | | | | | 50 | | | | | |
| Ergosterol | | | 30 | | | | | | | | | | |
| Stigmasterol | | | | 30 | | | | | | | | | |
| Campesterol | | | | | 30 | | | | | | | | |
| Spinasterol | | | | | | 30 | | | | | | | |
| Brassicasterol | | | | | | | 30 | | | | | | |
| Paraffin | | | | | | | | | 10 | 15 | 5 | 20 | |
| Evaluation results | A | B | A | A | A | A | A | A | A | A | A | B | A |

Comparative Examples 4 to 12

Preparation of Compositions for Comparison

Lipid compositions of Comparative Examples 4 to 12 were prepared by weighing predetermined amounts of the menthol and the comparative compounds described in Table 4 to realize the component ratios described in Table 4, mixing them in respective containers and then carrying out the operations in the same manner as in Example 1. The lipid compositions of Comparative Examples 4 to 12 were manipulated in the same manner as in Test Example 1, and their respective shape retention property was judged. The measured results are shown in Table 4.

In Table 4, the spherical nylon powder is SP-500 manufactured by TORAY INDUSTRIES, INC.

TABLE 4

| Comparative Example | l-Menthol | Cholesteryl stearate | Adamantane | Stearyl alcohol | Spherical nylon powder | Evaluation results |
|---|---|---|---|---|---|---|
| 4 | 90 | 10 | | | | D |
| 5 | 70 | 30 | | | | D |
| 6 | 90 | | 10 | | | D |
| 7 | 80 | | 20 | | | D |
| 8 | 70 | | 30 | | | C |
| 9 | 90 | | | 10 | | D |
| 10 | 80 | | | 20 | | D |
| 11 | 70 | | | 30 | | D |
| 12 | 99 | | | | 1 | D |

Examples 18 to 45

Preparation of Compositions

Lipid compositions were prepared by weighing predetermined amounts of the menthol and the materials described in Table 5 to realize the component ratios described in Table 5, mixing them in respective containers and then carrying out the operations in the same manner as in Example 1. The lipid compositions of Examples 18 to 45 were manipulated in the same manner as in Test Example 1, and their respective shape retention property was judged. The measured results are shown in Table 5.

In Table 5, LM indicates l-menthol, ST indicates cholesterol (manufactured by NIPPON FINE CHEMICAL), SE indicates Ceresine 810, CA 10 indicates 3-(1-menthoxy)propane-1,2-diol (manufactured by TAKASAGO INTERNATIONAL CORPORATION), the cooling agent base indicates an equimolar mixture of isopulegol, CA 10, CA 38 and glycol salicylate, CA 38 indicates p-menthane 3,8-diol (manufactured by TAKASAGO INTERNATIONAL CORPORATION), silicone indicates a cyclic dimethyl silicone (Silicone KF 995: manufactured by Shin-Etsu Silicone), PEG 6000 indicates polyethylene glycol 6000 and PEG 1000 indicates polyethylene glycol 1000.

TABLE 5

| Example No. | LM | ST | SE | CA 10 | Cooling agent base | Silicone | SP 5000 | PEG 6000 | MCW | PEG 1000 | Evaluation results |
|---|---|---|---|---|---|---|---|---|---|---|---|
| 18 | 75 | 17 | 6 | | | 2 | | | | | B |
| 19 | 75 | 10 | 10 | | 3 | 2 | | | | | B |
| 20 | 75 | 5 | 15 | | 3 | 2 | | | | | B |
| 21 | 75 | 6 | 16 | | 3 | | | | | | B |
| 22 | 70 | 14 | 14 | | 1 | | | | 1 | | B |
| 23 | 70 | 14 | 14 | | 1 | | 1 | | | | B |
| 24 | 70 | 14 | 15 | | | | 1 | | | | B |
| 25 | 70 | 14 | 15 | | 1 | | | | | | B |
| 26 | 70 | 10 | 19 | | 1 | | | | | | B |
| 27 | 70 | 10 | 17 | | 1 | | 2 | | | | B |
| 28 | 70 | 10 | 20 | | | | | | | | B |
| 29 | 70 | 10 | 17 | | 1 | | | | | 2 | B |
| 30 | 70 | 10 | 17 | | 1 | | | 2 | | | B |
| 31 | 70 | 17 | 10 | | 1 | | | 2 | | | B |
| 32 | 70 | 10 | 17 | | 1 | 2 | | | | | B |
| 33 | 66.5 | 30 | 3.5 | | | | | | | | A |
| 34 | 70 | 25 | 4 | | 1 | | | | | | A |
| 35 | 70 | 4 | 25 | | 1 | | | | | | A |
| 36 | 70 | 23 | 4 | | 1 | | | 2 | | | A |
| 37 | 70 | 23 | 4 | | 1 | | 2 | | | | A |
| 38 | 70 | 28 | | | 2 | | | | | | A |
| 39 | 70 | 28 | | 1 | 1 | | | | | | A |
| 40 | 70 | 26 | | 1 | 1 | | 2 | | | | A |
| 41 | 70 | 26 | | 1 | 1 | | | 2 | | | A |
| 42 | 75 | 23 | | 1 | 1 | | | | | | A |
| 43 | 73 | 23 | | 1 | 1 | | | 2 | | | A |
| 44 | 80 | 19 | | | 1 | | | | | | A |
| 45 | 80 | 18.5 | | | 0.5 | | | | 1 | | A |

The invention claimed is:

1. A lipid composition having a shape retention property such that its shape is maintained at the melting point of menthol, which comprises a menthol in an amount of from 50 to 90% by mass and a sterol in an amount of from 10 to 50% by mass.

2. The lipid composition according to claim 1, which further comprises a paraffin.

3. The lipid composition according to claim 2, wherein a content of the paraffin is 20% by mass or less based on the lipid composition.

4. The lipid composition according to claim 1, which further comprises one or more kinds of material selected from the group consisting of menthone, camphor, pulegol, 1-isopulegol, 3-(1-menthoxy)propane-1,2-diol, 2-(1-menthoxy)ethan-1-ol, 3-(1-menthoxy)propan-1-ol, 2-methyl-3-(1-menthoxy)propane-1,2-diol, 2-[(1-menthoxy)ethoxy]-ethanol, N-ethyl-1-menthylcarboxamide, p-menthane-3,8-diol, 1-menthyl lactate, N-methyl-(2,2-isopropylmethyl-3-methylbutanamide, vanillyl ethers, capsaicine, salicylic acid esters, mint oil, peppermint oil and spearmint.

5. The lipid composition according to claim 4, wherein the content of the material is 20% by mass or less based on the lipid composition.

6. A food or drink, which comprises the lipid composition according to claim 1.

7. A toiletry product, which comprises the lipid composition according to claim 1.

8. A fragrance or cosmetic, which comprises the lipid composition according to claim 1.

9. A bathing agent, which comprises the lipid composition according to claim 1.

10. A pharmaceutical, which comprises the lipid composition according to claim 1.

11. A tobacco, which comprises the lipid composition according to claim 1.

* * * * *